United States Patent [19]
Frantz et al.

[11] Patent Number: 5,237,309
[45] Date of Patent: * Aug. 17, 1993

[54] PUMP CASSETTE AND METHOD OF PUMPING

[75] Inventors: Mark G. Frantz, New York, N.Y.; Thomas J. Pavsek; Mark R. Honard, both of Mentor, Ohio; Lawrence M. Sears, Shaker Heights, Ohio; Ying Shen, Lyndhurst, Ohio

[73] Assignee: Frantz Medical Development, Ltd., New York, N.Y.

[ * ] Notice: The portion of the term of this patent subsequent to Jul. 4, 2006 has been disclaimed.

[21] Appl. No.: 368,375

[22] Filed: Jun. 19, 1989

Related U.S. Application Data

[63] Continuation of Ser. No. 75,627, Jul. 20, 1987, Pat. No. 4,845,487.

[51] Int. Cl.$^5$ .................. G08B 21/00; F04B 49/10; F04B 43/08
[52] U.S. Cl. ............................ 340/679; 417/63; 417/412; 417/566; 604/123; 604/153
[58] Field of Search .................. 340/679, 606–608, 340/626, 612, 619, 568, 636; 604/153, 67, 123; 137/493.1; 417/437, 566, 472–473, 63, 412–413; 92/130; 222/325

[56] References Cited

U.S. PATENT DOCUMENTS

| | | | |
|---|---|---|---|
| Re. 32,306 | 12/1986 | Waters | 604/165 |
| D. 278,743 | 5/1985 | Manno et al. | |
| D. 284,221 | 6/1986 | Kerkut | |
| 3,159,176 | 12/1964 | Russell et al. | 137/493.1 |
| 3,201,111 | 8/1965 | Afton | 604/133 |
| 3,650,093 | 3/1972 | Rosenberg | 55/159 |

(List continued on next page.)

FOREIGN PATENT DOCUMENTS

| | | |
|---|---|---|
| 0086731 | 8/1983 | European Pat. Off. |
| 1052614 | 12/1966 | United Kingdom |
| 2126666 | 3/1984 | United Kingdom |
| WO84-691 | 3/1984 | World Int. Prop. O. |

OTHER PUBLICATIONS

Ross Labs; Flexiflo-III Enteral Nutrition Pump; May 1985; Brochure D156.
Travenol Labs; Flo-Gard 200 Enteral Pump; Jan. 1985; Brochure 425601.
Vernay Labs; Combination Valves; 1985; Brochure 5 MPP885-Model VA 3836-See Spec. p. 13.

Primary Examiner—Glen R. Swann, III
Assistant Examiner—Thomas J. Mullen, Jr.
Attorney, Agent, or Firm—Frishauf, Holtz, Goodman & Woodward

[57] ABSTRACT

A medical pumping system has a supply tube (2), an outlet tube (6), a readily sterilizable, disposable cassette (3) connected to the tubes and engaged with the pump, and means (22,24) such as a motor-driven piston, for intermittently applying pressure to the cassette. The pumping system features a display and switch means (9, 10) on a front panel thereof, a pressure sensor (28), an optical fluid presence sensor (19), and a microprocessor (20) metering the volume of fluid pumped through said cassette (3), monitoring output signals from said sensors (18, 28), controlling the motor-driven piston in accordance with settings entered via said switch means (9,10), and directing output data to said display means (8). The microprocessor has a stored program for performing SET RATE, RUN, HOLD, VOLUME FED, and CLEAR VOLUME functions. The cassette includes a hydraulically self-actuating inlet valve (44) communicating with the supply tube (2), a hydraulically self-actuating outlet check valve (42) communicating with, and preventing backflow from, the outlet tube (6), a hollow, resilient compressible member, such as a bellows (34) having an interior communicating with the inlet and outlet valves, and a support structure (30,36,38) securing together the tubes, valves and bellows in operating relation. Preferably, the inlet and outlet valves are a unitary element.

18 Claims, 16 Drawing Sheets

U.S. PATENT DOCUMENTS

| | | | |
|---|---|---|---|
| 3,985,133 | 10/1976 | Jenkins et al. | 604/67 |
| 3,994,294 | 11/1976 | Knute | 604/152 |
| 4,030,495 | 6/1977 | Virag | 604/123 |
| 4,060,178 | 11/1977 | Miller | 417/473 |
| 4,067,332 | 1/1978 | O'Leary | 604/152 |
| 4,080,967 | 3/1978 | O'Leary | 604/152 |
| 4,084,606 | 4/1978 | Mittleman | 137/102 |
| 4,126,132 | 11/1978 | Portner et al. | 604/123 |
| 4,157,092 | 6/1979 | Faré et al. | 128/202.27 |
| 4,256,437 | 3/1981 | Brown | 417/63 |
| 4,391,599 | 7/1983 | Jenkins | 604/118 |
| 4,392,858 | 7/1983 | George | 604/133 |
| 4,396,385 | 8/1983 | Kelly et al. | 604/152 |
| 4,457,753 | 7/1984 | Pastrone | 604/153 |
| 4,515,591 | 5/1985 | Hemmerich et al. | 604/152 |
| 4,519,792 | 5/1985 | Dawe | 604/123 |
| 4,536,139 | 8/1985 | Greco | 417/471 |
| 4,537,561 | 8/1985 | Xanthopoulos | 417/63 |
| 4,578,060 | 3/1986 | Huck | 604/133 |
| 4,639,197 | 1/1987 | Tornare | 417/259 |
| 4,642,088 | 2/1987 | Günter | 604/133 |
| 4,845,487 | 7/1989 | Frantz et al. | 340/679 |
| 4,850,807 | 7/1989 | Frantz | 417/63 |

PUMP CASSETTE AND METHOD OF PUMPING

This application is a continuation of application Ser. No. 07/075,627, filed July 20, 1987, now U.S. Pat. No. 4,845,487, issued Jul. 4, 1989.

Cross-reference to related patent, the disclosure of which is hereby incorporated by reference: U.S. Pat. No. 3,159,176, RUSSELL & BIFFORD issued Dec. 1, 1964 and assigned to Vernay Laboratories, Inc.

Cross-Reference to related applications, the disclosures of which are incorporated by reference:

DISPOSABLE CASSETTE FOR FLUID DELIVERY PUMP SYSTEMS, Frantz, Ser. No. 07/062,905, filed Jun 16, 1987, now U.S. Pat. No. 4,850,807, issued Jul. 25, 1989;

COMPACT PUMP SYSTEM FOR FLUID DELIVERY, Mark G. Frantz, Design Ser. No. 07/063,275, filed Jun 16, 1987, COMPACT POWER & POLE CLAMP ASSEMBLY FOR COMPACT FLUID DELIVERY PUMP SYSTEM, Mark G. Frantz, Design Ser. No. 07/063,274, filed Jun 16, 1987, ROTATIONAL CONTROL DIAL WITH FLUSH/PROTRUDING FLIP HANDLE, Mark G. Frantz, Serial No. 07/080,643, filed Jul. 16, 1987, DISPOSABLE MEDICAL PUMP CASSETTE, Mark G. Frantz, Design Serial No. 07/063,273, filed Jun. 16, 1987.

The present invention relates generally to fluid delivery systems for the administration of nutrients to humans or animals. More particularly, the invention relates to a new, improved volumetric fluid pumping system incorporating a disposable, sterilizable cassette with an internal self-actuated valve system, which may be reliably and easily inserted into, and removed from, a pump housing by relatively untrained medical personnel or unskilled patients.

BACKGROUND

It is common medical practice to deliver nutritional fluids either enterally through the alimentary canal via a naso-gastric tube or a jejunostomy catheter, or parenterally via an intravenous catheter. Medical personnel generally utilize positive pressure pumps to deliver and regulate the flow of these nutrients.

Conventional enteral pumps are non-volumetric, positive-pressure peristaltic systems utilizing silicone rubber tubing inserts, which are in direct contact with the pump rotor, and which, in turn, are mechanically connected to the PVC tubing linking the fluid reservoir and patient to the pump. The silicone rubber insert is stretched around the rotor by means of mounting tabs which are positioned in slots or brackets on the pump face. The tubing sets also embody drip chambers which are mounted inside optic path housings in order to observe the passage of fluid drops, thereby detecting nutrient flow or the absence of flow.

The intrinsic design of these peristaltic enteral pumps results in a number of functional drawbacks, most notably: volumetric inaccuracies under many common operating conditions, unsafe operating conditions if the set is not properly mounted on the pump, and complicated set assembly techniques.

The accuracy of peristaltic pumps is greatly affected by the pressures exerted by the fluid reservoir and patient height relative to the pump, by the fluid viscosity, and by the physical properties of the silicone insert. These are non-volumetric systems as compared to positive displacement volumetric systems such as syringe pumps, and do not embody valving systems, which results in exogenous pressures affecting the overall flow rate. The use of expensive silicone rubber inserts has been necessary in order to maintain accuracy and avoid deterioration and splitting of the tubing over even relatively short periods. The silicone tubing must be extruded to very tight inner diameter and outer diameter tolerances and requires very precise cutting and overall length assembly within the mounting tabs.

The assembly process is further complicated because silicone is not compatible with plastic bonding techniques. This problem also creates the possibility of leakage at the attachment joints if the set is pressurized due to a downstream occlusion. The mounting of these sets has always been an acknowledged problem. Patients and medical personnel have often incorrectly mounted the sets on the pump face resulting in no flow, inaccurate flow, or in some cases, even open flow, which may cause severe patient complications. The mounting of the drip chambers within optic path housings is also an acknowledged problem, resulting in false alarm situations. The use of optic path flow detection also restricts the use of these pumps to relatively upright, motionless applications; otherwise, the fluid drops may bypass the optics beam, or may splash on the side walls and coat the walls, falsely blocking the optics beam.

Many parenteral drop flow controllers or infusion pumps are susceptible to the same types of problems as the enteral pumps. Even the more advanced, expensive, positive-pressure, volumetric syringe types perform in less than a satisfactory manner in several respects. These devices are generally complicated to operate, and allow for incorrect mounting of the disposable cartridges. These problems are documented and have even been the subject of discussion in new patent applications.

The major obstacle to proper mounting of the cartridges is the attachment of the syringe head to the pump piston mechanism. This design restriction has been documented to cause misalignment, which may even allow air or pathogens to enter into the syringe fluid chamber, as well as to cause inaccurate flow rates. It has also been reported that various valving mechanisms and alarm detector interfaces have been improperly mounted in the pump bodies.

A second major limitation of these devices is their lack of appropriateness for enteral nutritional administration. Generally these devices and the disposable cartridges are very expensive compared to enteral products, and require sophisticated trained personnel for proper operation. In addition, several cartridge designs allow for the accumulation of enteral nutrient residue in the valving inlets/outlets, which over time will adversely affect the flow rates and volume delivered.

As a result of the current state-of-the art limitations of the enteral and parenteral nutrient pump systems, a clear need exists to provide the medical community with an accurate, safe, cost-effective system which may be reliably utilized by relatively unsophisticated patients and personnel in a wide range of settings, including ambulatory and home care. The invention set forth below intrinsically fulfills this need.

THE INVENTION

Accordingly, it is among the objects of the present invention to increase the accuracy and safety of the pumping system, lower the cost of the system components and the cost of assembling them, reduce the skill and time required to set up the system for use by or on a patient, and allow the pump system to be used in an ambulatory mode.

Briefly, the present invention replaces the conventional peristaltic rotor/silicone tubing combination and syringe-type infusion pump systems with a cassette containing a compressible membrane and at least one pressure-actuated check valve. The disposable, sterilized cassette is inserted into a pump housing at a location adjacent to a reciprocating piston which drives the compressible membrane. Sensors are located within the pump chamber and are connected to a monitoring circuit in the pump housing for the purpose of alerting the user to any malfunctions or other alarm conditions. Preferably, a microprocessor is employed for monitoring purposes, setting desired flow rates, metering, and generating alarm indications.

More particularly, the present invention provides greater accuracy under a wide range of specific operating conditions, compared to many peristaltic systems, as a result of the volumetric design and the use of both an upstream and downstream valving system. The operating accuracy in the medical environment should also be improved due to the simplicity of set-up in the present invention, compared to currently available enteral and parenteral pump systems.

The present invention also provides enhanced safety due to its sealed cassette, and downstream check valve which will prevent fluid leakage, open flow of the nutrient, and the intake of air or pathogens. Safety will also be improved by the reduction in potential operator error, as the cassette simply snap-fits into place, and there are no drip chamber compartments or valve mechanisms to load. Furthermore, if the cassette is not properly locked into place, by inserting the cassette into the pump chamber past the latching mechanism, the compressible membrane will return the cassette to a position substantially outside of the pump and a pressure sensor alarm will be activated if the pump is put into the run mode. The latching mechanism also prevents accidental dislodging during use, which in a valveless peristaltic system could result in open flow.

The elimination of silicone tubing, and the inherent design of the present invention's cassette reduce the complexity of set production. The cassette is composed of all molded pieces, which are easily press-fit, sonic-welded or adhesively bonded together. There is no silicone tubing to be cut to extremely precise tolerances and there are no plastic-to-rubber joints requiring special treatment to avoid fluid leakage. Also, the pumping mechanism does not require expensive linkage systems, optic path compartments for drip chambers, or external valving actuators.

Mounting of the cassette into the circular pump chamber is an easy operation, not requiring unusual dexterity or training. The arrow-shaped cap fits into an identically shaped indentation in the pump housing, and the latching system is self-actuating. There are no drip chambers or external valves to be mounted.

The replacement of drip chamber sensors with new and improved pressure sensors and an optics sensor across the body of the cassette allow the present invention to be used in a totally ambulatory mode, i.e. the patient can walk around.

These features of the present invention fulfill well recognized needs in the medical community for a versatile, easy-to-use, safe and accurate nutritional fluid pump system. These advantages will be further obvious from the following detailed description and the accompanying drawings. The following detailed description of the preferred embodiment specifically relates to an enteral pump system; however, the invention may also easily be adapted for parenteral use by the addition of air bubble detectors or eliminators, of which many are known in the art.

DRAWINGS

These and other advantages of the present invention will be apparent from the drawings, in which.

DETAILED DESCRIPTION

Figure 1:
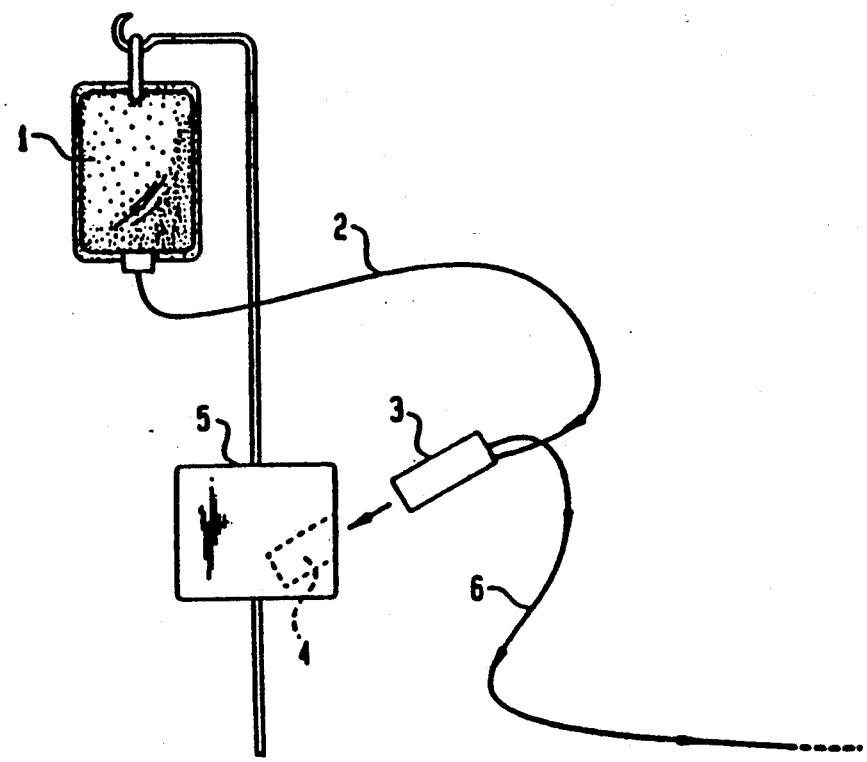
FIG. 1 is a schematic view of a pumping system, showing the nutrient reservoir, the tubing leading therefrom, the bellows cassette, the pump-and-control housing into which the cassette is inserted, and the tubing from the cassette toward the patient.

FIG. 1 illustrates the overall pumping system of the present invention. Nutrient flows from a reservoir 1, either hung on an intravenous pole or worn on the patient, down a pump supply tube 2 and into a cassette 3. Preferably, cassette 3 includes a resilient bellows, but other hollow, compressible elements, such as a rubber dome or a spring encased in a collapsible membrane, could be used and are within the scope of the present invention. During operation, cassette 3 is secured within a chamber 4, indicated by dotted lines, within a pump-and-control housing 5. Preferably, chamber 4 is angled about 30° with respect to the pump housing. If supply tube 2 contains any air bubbles, they will tend to rise and be purged. After pumping, solution flows from cassette 3 through pump outlet tube 6 into the patient.

Figure 2:
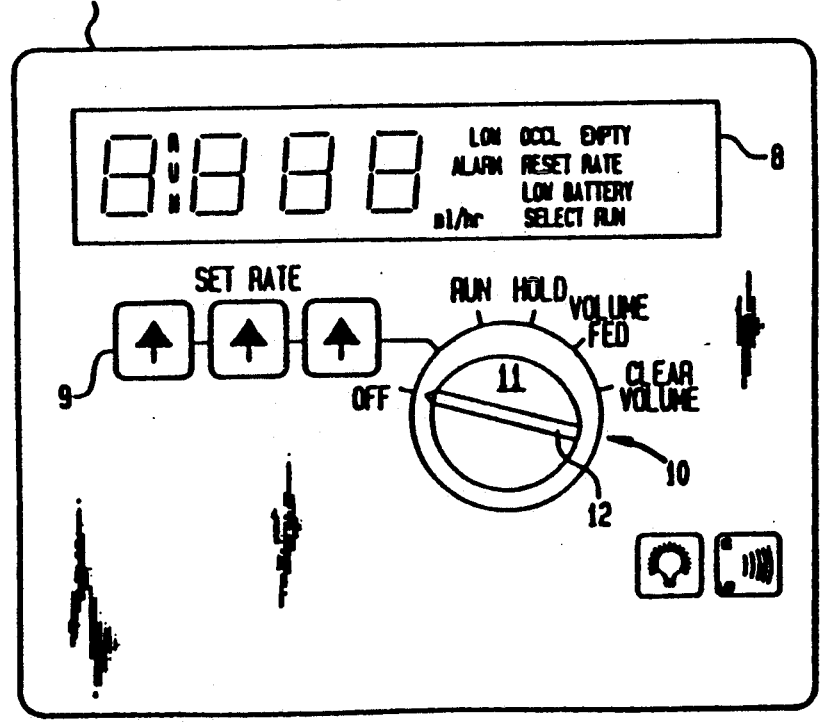
FIG. 2 is a front view of the pump-and-control housing, including the novel flip-handle control setting means thereof.

FIG. 2 illustrates the front control panel of the pump housing 5. It features a display window 8, preferably comprising alarm indicators and standard seven-segment displays such as liquid crystal displays (L.C.D) or light-emitting diodes (L.E.D). A suitable LCD is Hamlin model 4717315431. A plurality of buttons 9, preferably membrane switches, permit adjusting the numbers shown in window 8. A novel flip-handle control dial 10 is provided for switching between the modes indicated by the legends on the drawing. A half-spherical recess 11 is provided in the face of the pump housing and permits a disk-shaped handle 12, which is pivotally secured at two of its opposing edges, to be push-pivoted into recess 11. Handle 12 is secured in a dial housing attached to pump housing 5. The dial housing is attached to a multi-position switch, whose six contacts are illustrated at the lower left corner of FIG. 14. The user can place one finger on each face of disk 12 and rotate the disk about a horizontal axis, thereby closing respective switch contacts located, for example, on a printed circuit board (PCB) mounted within housing 5. When the desired setting is reached, disk 12 can be pivoted back flush with the housing surface, leaving no projecting elements to be snagged. by an ambulatory patient's clothing, tubing, or the like. This also reduces unauthorized manipulation of the controls.

Figure 3:
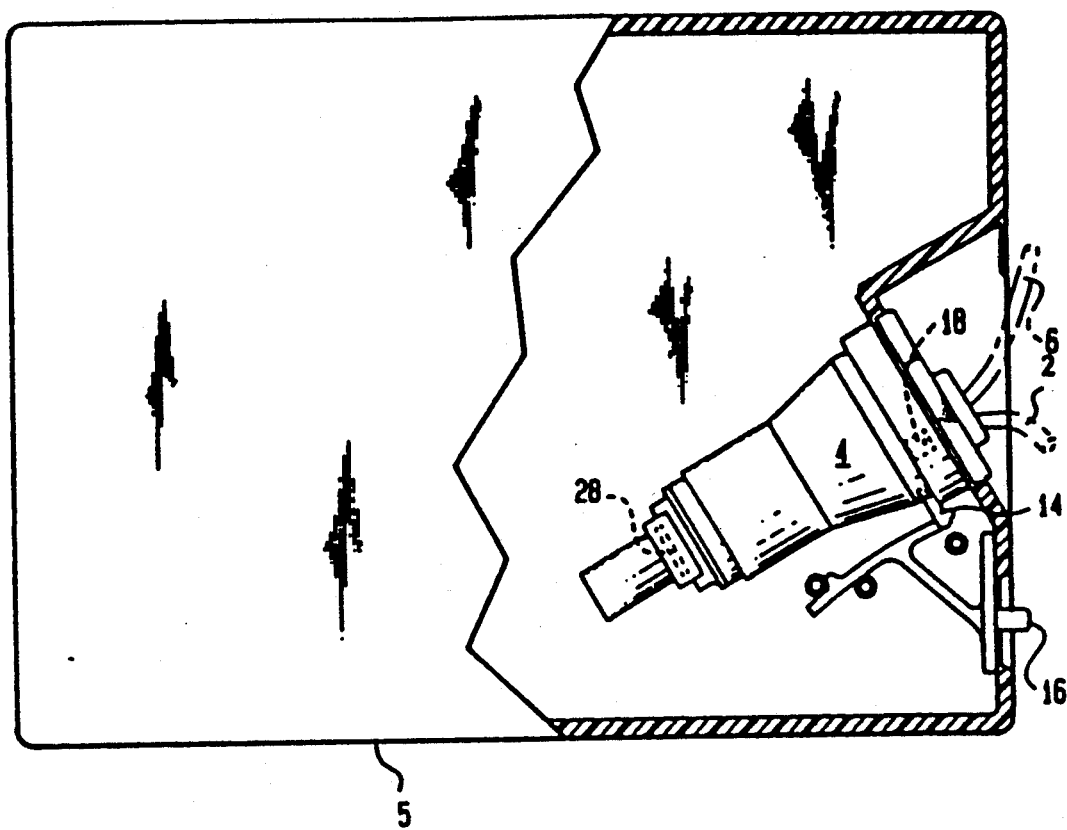
FIG. 3 is a vertical cross-section through the pump housing and the cassette-receiving chamber therein.

FIG. 3 is a vertical cross-section through pump housing 5, showing a cassette-receiving chamber 4 and other components. The cassette is releasibly secured within chamber 4 by a latch 14, preferably spring-loaded, and released by a sliding handle 16 on the exterior side surface of housing 5. An optical emitter 18, disposed within the wall of a chamber 4 into which cassette 3 is inserted, emits a light beam into one side of cassette 3 and an optical decoder 19 on the opposing side of cassette 3 detects when a chamber 39 within cassette 3 is empty of fluid and causes an alarm to sound. Suitable components 18 and 19 are the TRW Optron #OP240 SLA GaAlAs plastic infrared emitting diode and the TRW Optron #OP550 SLC NPN silicon photo-transistor, both operating at a wavelength of 880 nanometers.

Figure 15:
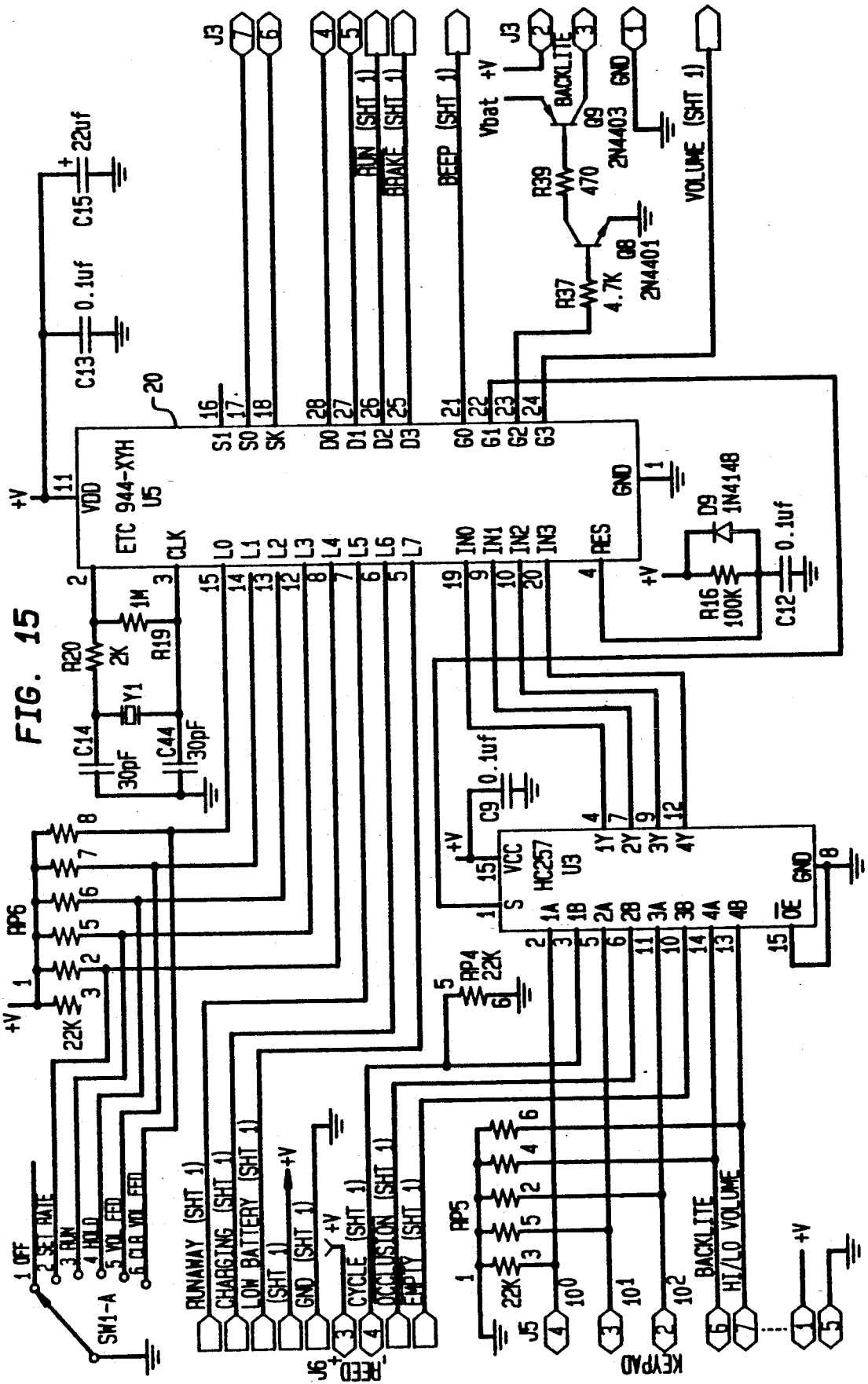

A microprocessor 20, preferably a Thomson/Mostek model ETC 944N-XYH or a National Semiconductor model COP444CN, is shown in FIG. 15 and is connected to all electrical elements in the pump housing, and responds to sensor input signals by generating appropriate control output signals in accordance with its program.

In particular, microprocessor 20 generates control pulses for rotation of a motor 22, which rotates a cam and thereby causes a cam follower or piston 24 to compress the bellows portion of cassette 3. Motor 22 is preferably a DC gearmotor such as model 1624E003SP42+16/5, 262:1 K297 from MicroMo Electronics. Of course, an equivalent element, such as an eccentric cam, could be used in place of piston 24, with minor modifications. Microprocessor 20 controls window 8's seven-segment display driver 26, which is preferably a National Semiconductor model COP472N-3. Microprocessor 20 also monitors switches 9, control dial 10, optical detector 19, battery energy level, and a pressure sensor 28. Pressure sensor 28 is preferably a piezo-electric disc transducer, such as model PZT-5A #6020 from the Vernitron Piezoelectric division, and detects the pressure between bellows 34 and piston 24.

Microprocessor 20 processes the shape of the curve of the variation of pressure with time to detect whether a blockage or break in the tubing has occurred. The system can distinguish the following conditions: (1) an empty cassette-receiving chamber; (2) an upstream blockage or occlusion in supply tube 2; and (3) a downstream blockage or occlusion, such as the patient kinking output tube 6. In the case of an upstream occlusion, the typical bell curve described by the pressure signal from the transducer 28 is shifted some milliseconds later in time with respect to the motor cycle and piston movement. In the case of a downstream occlusion, the peak of the pressure curve is higher than the normal voltage signal peak of about 1.2 volts. Electrical power is supplied by a battery 29, preferably of the 4-volt variety. The microprocessor's memory preferably includes 128 bytes of RAM (Random Access Memory) and 2 kilobytes of ROM (Read-Only Memory), preferably containing the operating program whose flow charts are shown in FIGS. 7-13.

Figure 4:
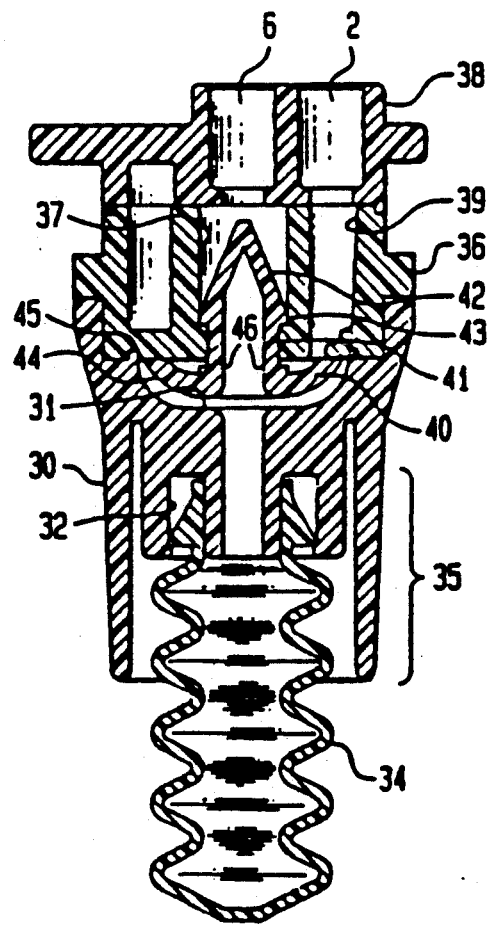

FIG. 4 is a cross-sectional view of cassette 3. The cassette includes a generally cylindrical retainer 30, having at one end a bowl-shaped recess 31, and at the other end an annular chamber 32, into which fits the single open end of a compressible element 34, such as an axially corrugated, generally cylindrical bellows. A tubular protective shroud 35 portion of retainer 30 has a somewhat larger diameter than bellows 34 and surrounds the bellows for a portion of its length. The other end of bellows retainer 30 interfits with, and is secured to, a valve retainer 36 having a generally cylindrical exterior, a central axial passage 37 and an off-center axial passage 39. The interfit may take the form of an annular groove and matching annular rib. Plastic material is used to reduce weight, and other semi-annular recesses may be provided, as shown.

Figure 3A:
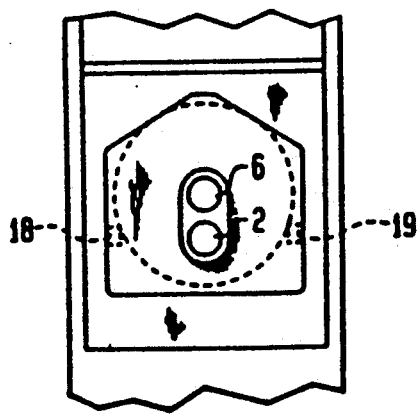
FIG. 3A is an schematic side view of the pump housing and the irregularly-shaped cassette cap mating therewith, and showing the location of the optical sensing system components.

A cassette cap 38, forming apertures for receiving pump supply tube 2 and output tube 6, is secured to the end of valve retainer 36 remote from bellows retainer 30. The periphery of cap 38 preferably has an irregular shape, as shown in FIG. 3A, so that it will fit into housing 5 in only one orientation, thereby preventing erroneous mounting of cassette 3. Preferably, these elements comprise styrene acrylonitrile (SAN) or similar rigid thermoplastic, and are secured together by sonic welding at a frequency of 20,000 Hertz or by adhesives.

Bellows 34 preferably comprises ethyl vinyl acetate (EVA) and is injection blow-molded.

Contained between retainer 30 and valve retainer 36 is a combination valve 40, preferably of a silicone-based material. Valve 40 has a central tubular portion or stem 41, which extends into axial passage 37 of valve retainer 36, containing a duck-bill check valve 42 which prevents backflow of solution away from the patient toward the pump. Valve 42 closes under back-pressure in pump output tube 6 thus prevents backflow, regardless of whether the pump is operating or how the pump, supply reservoir, and tubing are oriented with respect to the patient. Extending from stem 41 is an umbrella valve 44, with its outer peripheral rim 45 pointing away from bellows 34 and toward supply tube 2. Between valves 42 and 44, stem 41 has an outwardly extending annular rib 43, which interfits with a radially inwardly extending annular rib of valve retainer 36.

Operation

Valve 44 opens under a pressure of about 85 inches of water as the "umbrella rim" 45 flexes away from central portion 41, deeper into bowl-shaped recess 31, and permits fluid to flow from tube 2 into the cavity defined by bowl-shaped recess 31 and bellows 34, as bellows 34 expands due to its inherent resiliency. Rib 43 on stem 41 prevents valve 40 from sliding axially. Thereafter, compression of bellows 34 forces a repeatable, metered volume of its contents, preferably about one-third cubic centimeter of fluid, out through central axial aperture 46, duck-bill valve 42 and passage 37 into tube 6. The repetition or pulse rate of these compressions is varied to obtain the desired flow rate.

Valves 42 and 44 are self-actuating and require no external controls, linkages, solenoids, or the like. Their opening and closing is timed exactly by the fluid flow. This substantially improves accuracy, simplifies the construction, increases reliability, and reduces cost. Valve 40 is press-fitted into valve retainer 36. In searching for an appropriate design for valve 40, I recognized that a prototype combination valve shown as model VA 3836 in a catalog from Vernay Laboratories, Inc. of Yellow Springs, Ohio would provide the needed functionality. The basic design of this valve is set forth in U.S. Pat. No. 3,159,176. After some research and development, including adjustment of the "cracking pressure" of the valve, such a valve design was found to be satisfactory. The shape and the pre-loading of the umbrella 44 are important features. Preferably, as set forth above, they are chosen so that valve 44 opens at a pressure somewhere above about 85 inches of water.

Bellows 34 simultaneously serves as a metering chamber and performs four functions:
(1) opening inlet valve 44;
(2) sucking in a metered volume of fluid;
(3) providing a return force; and
(4) opening the distal or outlet valve 42 to eject fluid.

The fact that bellows 34 is self-returning means that no attachment of it to the reciprocating element is necessary, unlike prior art syringe pump elements, so that setting up by patients or nurses may be rendered error-free. Bellows 34 is press-fit to bellows retainer 30 and may be further secured by an adhesive, preferably a cyano-acrylic such as Loctite Pyramid 460 Cyanoacrylate, which is water-resistant.

Figure 5:
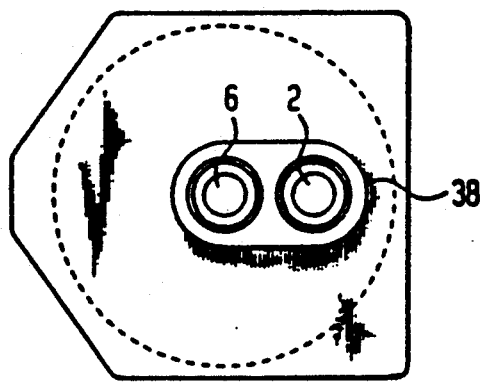
FIG. 5 is an end view of the bellows cassette showing the and outlet tubes thereof.

FIG. 5 is an end view of cassette 3, showing that supply tube 2 preferably connects into an off-center aperture to cassette cap 38, while output tube 6 fits centrally. The periphery of cap 38 preferably has an irregular shape, such as the irregular polygon or "arrow" shape shown in FIG. 5, so that it will fit into housing 5 in only one orientation, thereby preventing erroneous mounting of cassette 3 by a relatively unskilled patient or an inadequately trained health care employee. The cassette will not latch into the housing if improperly inserted, and the pressure sensor will cause an alarm to be generated within a predetermined number of motor cycles.

Figure 6:
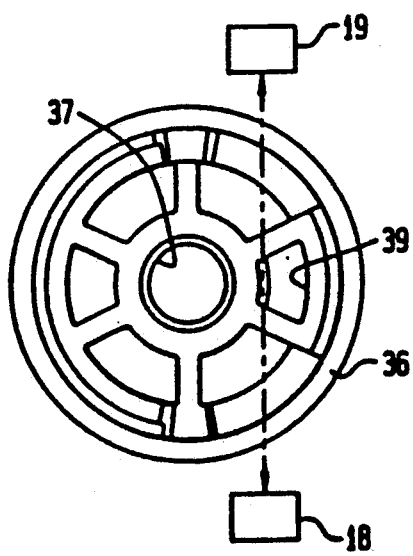
FIG. 6 is cross-section along line VI—VI of FIG. 4, illustrating the invention's optical empty-detection system.

FIG. 6 is a cross-sectional view of the optical system. Two wedge-shaped radial sections of element 36 are cut away or formed with recesses. Emitter 18 directs a beam of light through one of these sections of cassette 3 toward detector 19, which is adjacent the other of these recesses. If fluid is in the path of the beam, the light scatters and is attentuated below a threshold set for the detector signal; if supply tube 2, and thus chamber 39, runs empty, the light is not scattered, detector 19 is triggered, and an alarm indication is generated. Preferably, the word "empty" is illuminated on the LCD window 8 and a beeper sounds.

Figure 7:
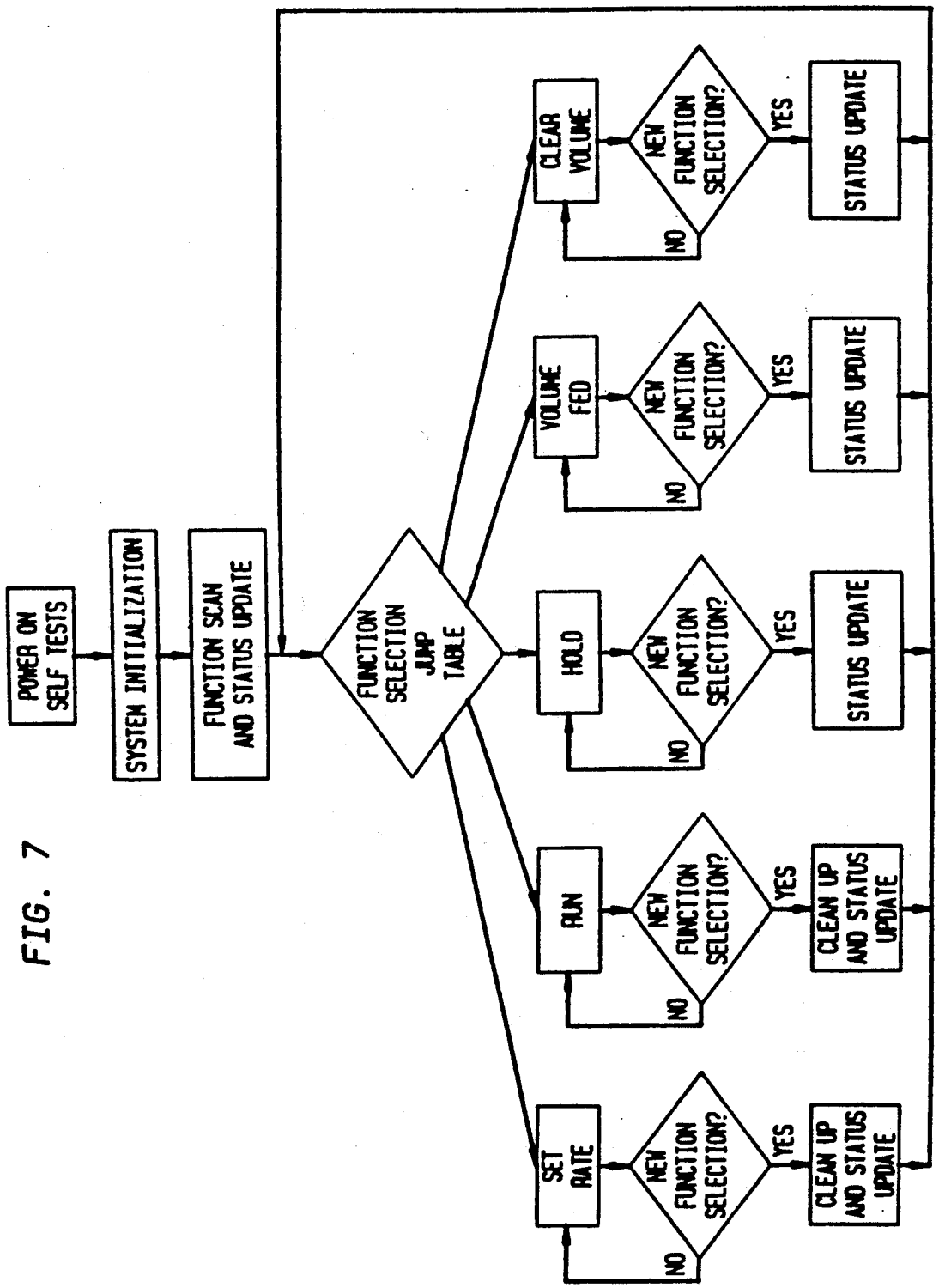
FIGS. 7-13 are flowcharts of the operational sequence or program of the system.

FIG. 7 is a flow chart of the overall structure of the preferred operating program for microprocessor 20 and its associated components. The function scan step detects where the rotating switch shown on FIG. 2 is positioned. The function selection jump table transfers control to the subroutine corresponding to that one of the five functions which has been selected on the control dial.

Figure 8:
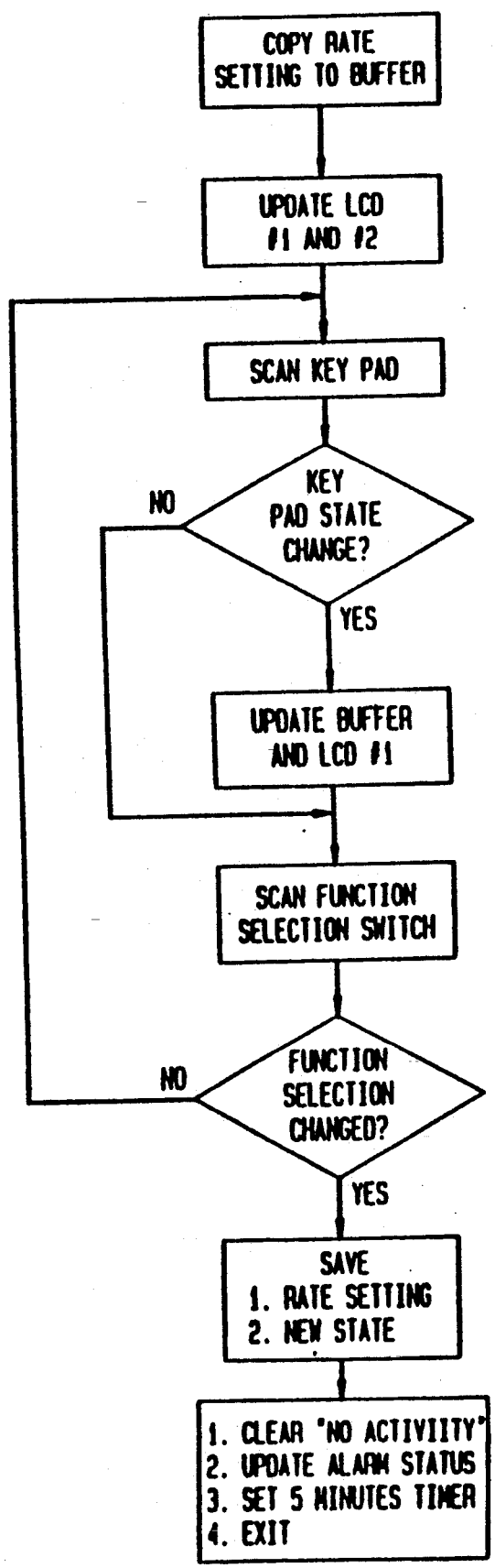

FIG. 8 illustrates the subroutine to SET RATE, that is, to determine how fast the fluid will be pumped, within the preferred operating range of 5-300 milliliters per hour.

Figure 9:
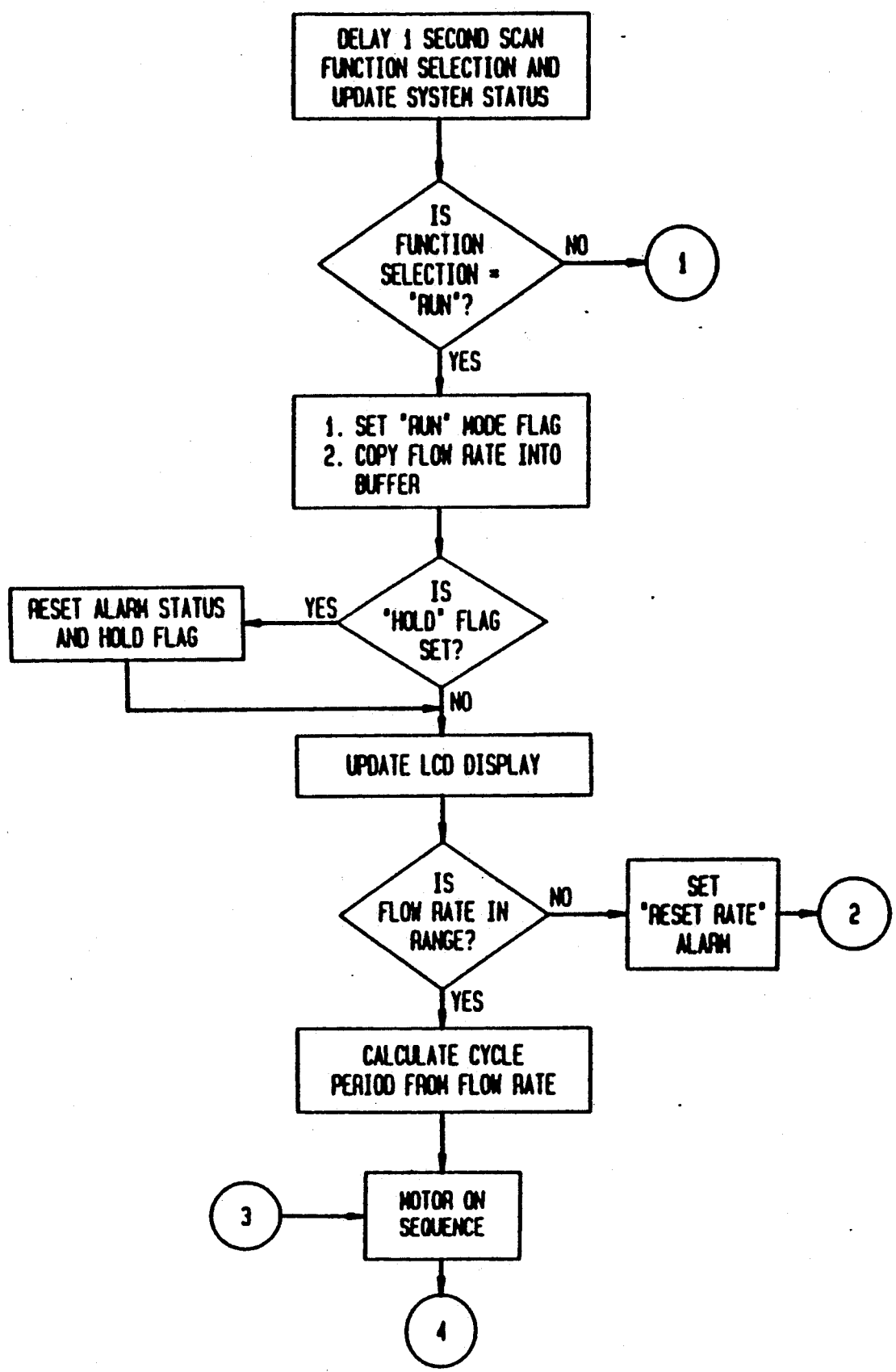

FIG. 9 illustrates the first part of the RUN subroutine, for actually starting pumping at the chosen rate.

Figure 10:
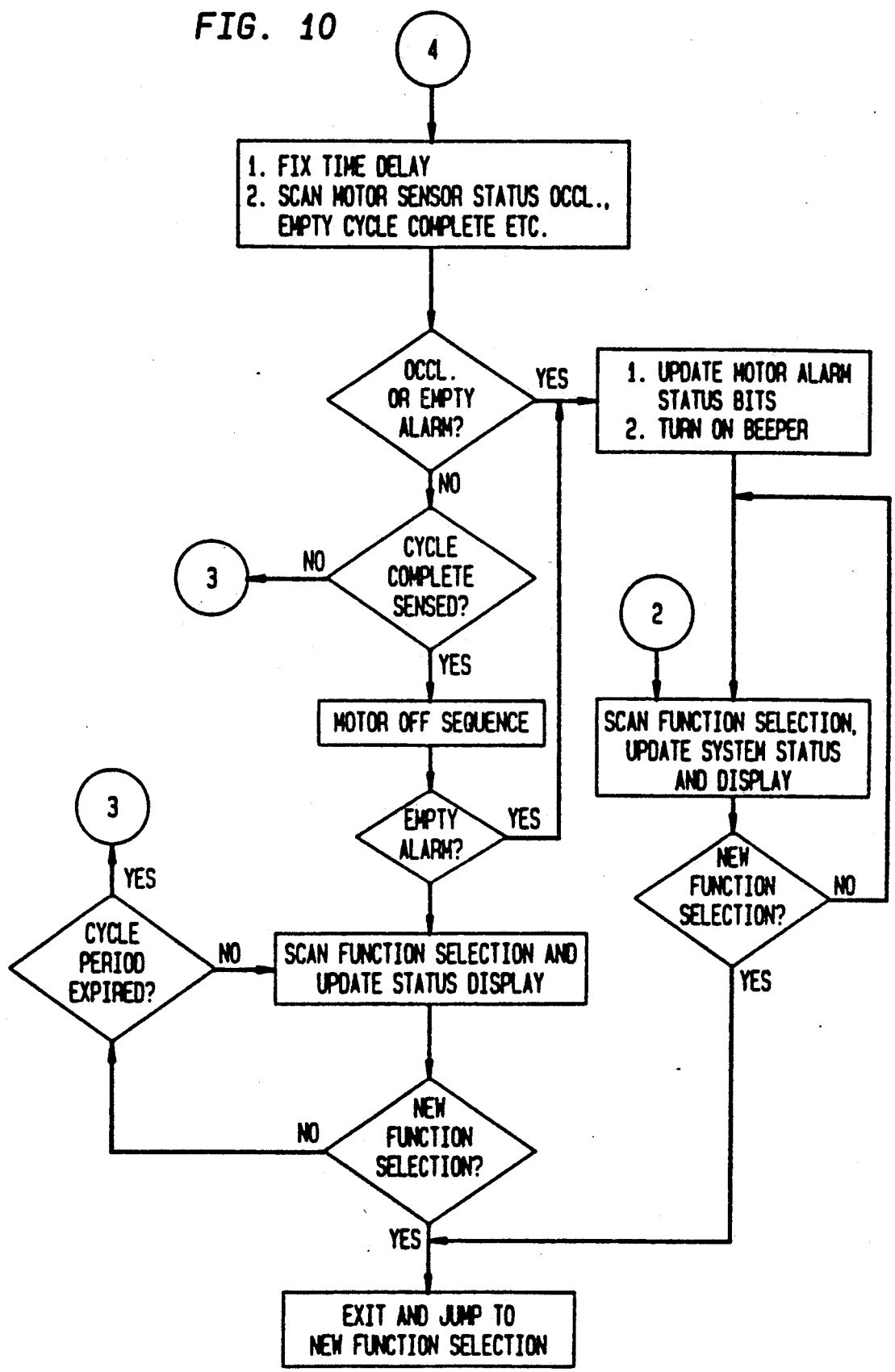

FIG. 10 illustrates the second part of the RUN subroutine, for monitoring sensors to determine if any alarm indications should be generated.

Figure 11:
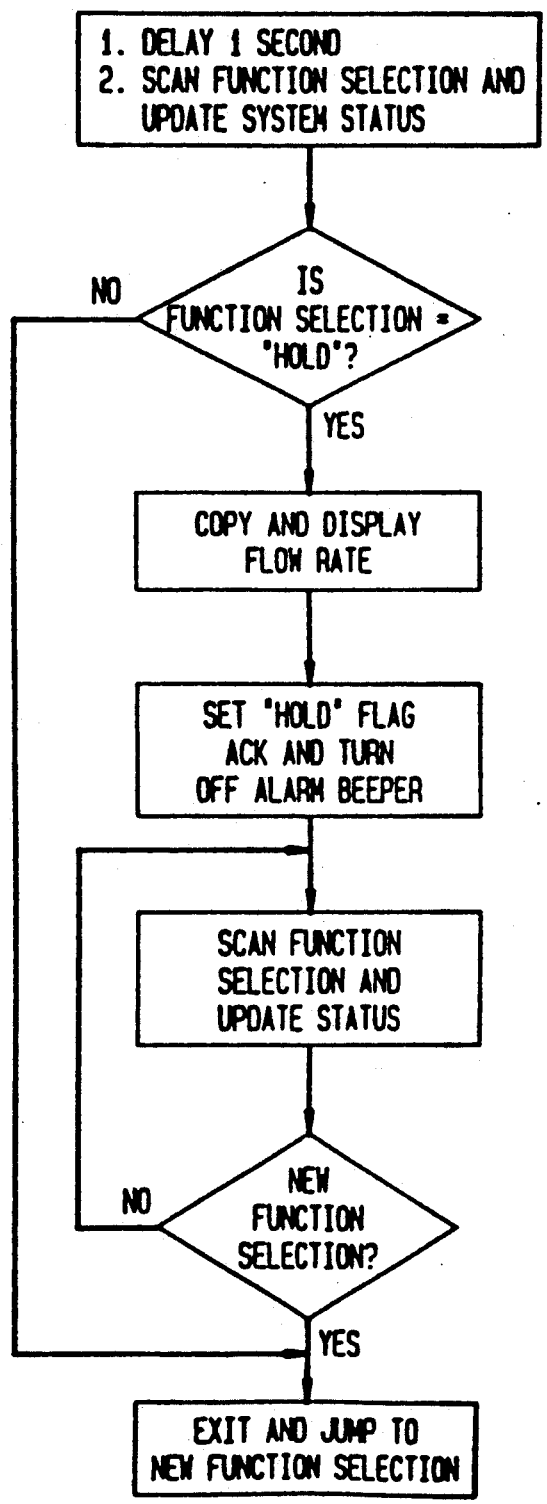

FIG. 11 illustrates the HOLD subroutine, for preserving the data on the volume of fluid fed to the patient while deciding which function or rate to set next.

Figure 12:
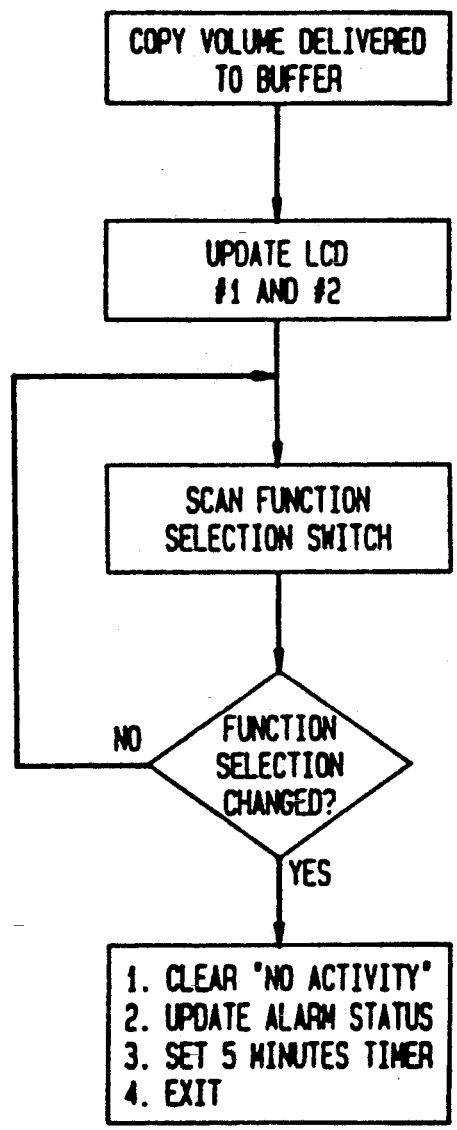

FIG. 12 illustrates the VOLUME FED subroutine. It is noteworthy that this subroutine, as well as the HOLD, SET RATE, and CLEAR VOLUME subroutines, cause an audible alarm if the pump is left unattended for 5 minutes. This prevents patient neglect and preserves battery power.

Figure 13:
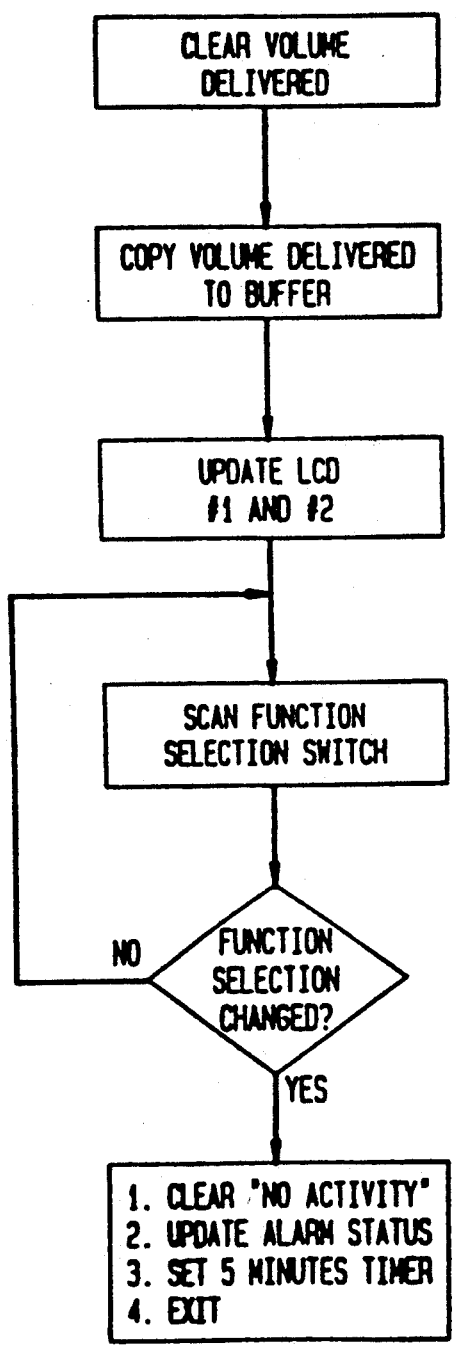

FIG. 13 illustrates the CLEAR VOLUME subroutine, for erasing the data on the volume of fluid fed.

Figure 14A:
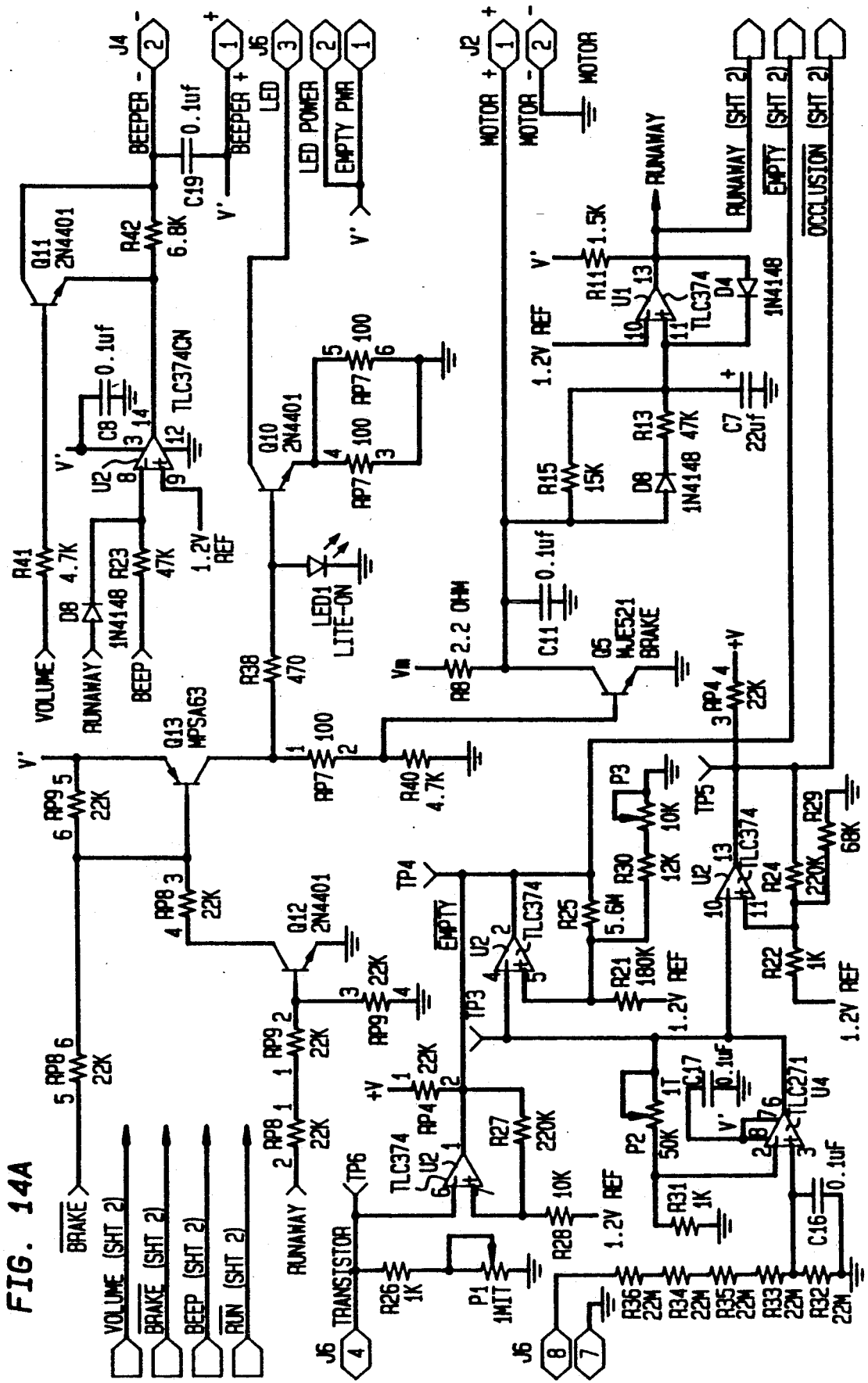
FIGS. 14A-16 are schematic views of the pump circuits.
Figure 14B:
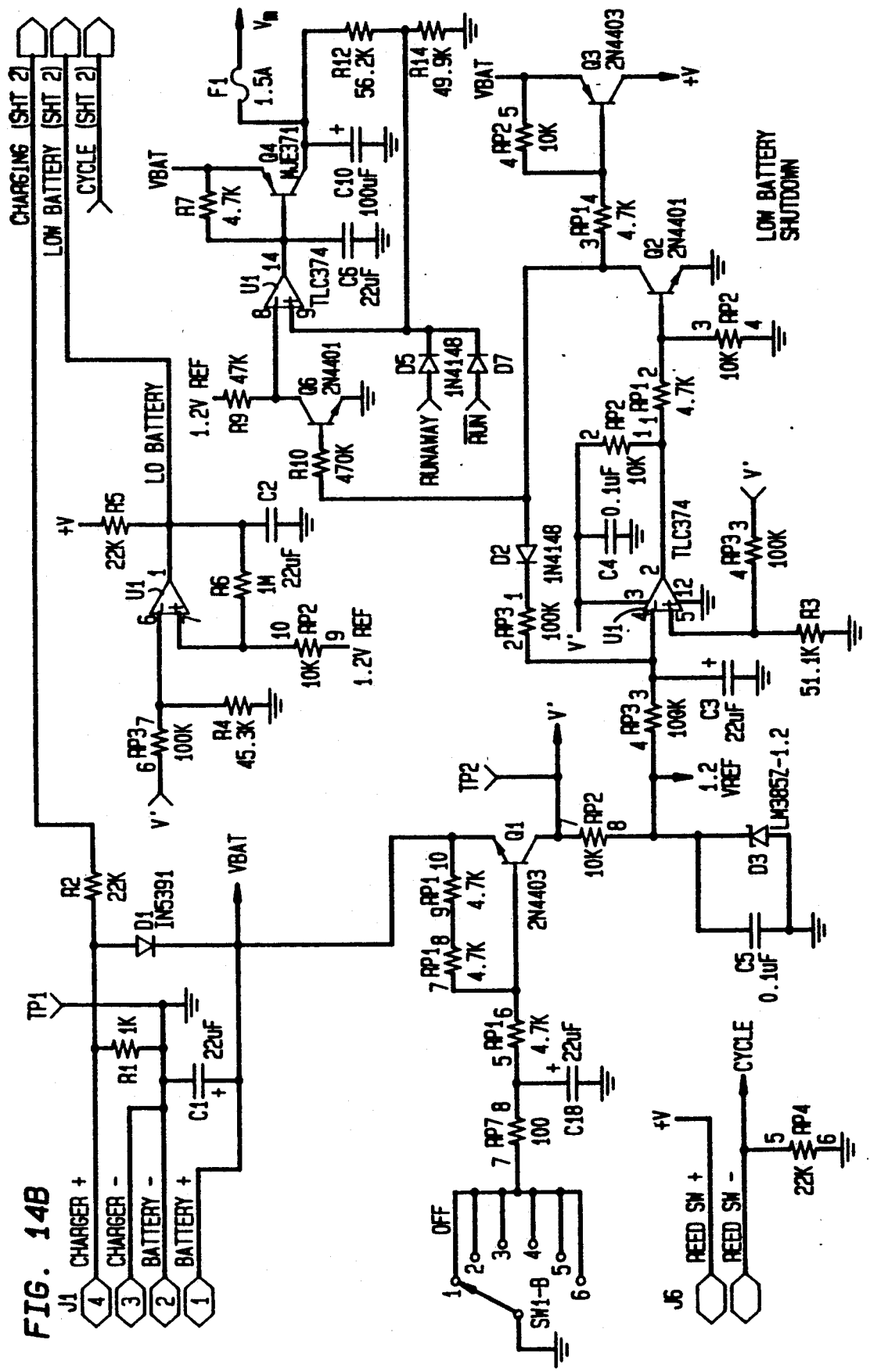

FIG. 14a is sheet 1 of the circuit diagram of the pump circuit. Beginning at lower left, FIG. 14B shows a reed switch which detects the passage of a magnet (not shown) which rotates with the shaft of motor 22. This generates a CYCLE signal which goes into the pin 1B of the multiplexer shown in FIG. 15, and thereby tells the microprocessor 20 when each motor rotation occurs.

Just above the reed switch, the contacts for rotary switch 11-12 are shown. A capacitor C18 and associated resistors serve to "de-bounce" the switch contacts.

Above the rotary switch contacts, the charging circuit, including diode D1, is shown. This circuit supplies Vbat for Powering other parts of the circuit. A signal goes through resistor R2 to pin L6 (FIG. 15) of microprocessor 20 to indicate when power is coming from the charger in a pole clamp assembly or backpack (not shown) rather than from the battery.

Downstream of diode D1, a circuit including transistor Q1 supplies voltage V' which supplies all of the comparators and the operational amplifier in the rest of the circuit. This voltage is typically in the range between about 3.65 volts and about 4.5 volts.

Further downstream, in the lower middle portion of FIG. 14B, a low-battery shutdown circuit, including a first comparator U1 and transistors Q2 and Q3 acting as switches, shuts down the circuit and latches whenever voltage V goes below 3.65 volts. As a safety feature, the circuit cannot be restarted without turning off the pump.

Further to the right in the lower portion of FIG. 14B, a circuit including a transistor Q3 supplies a voltage V+ which powers microprocessor 20, the multiplexer, the occlusion detector circuit of FIG. 14, to be described below, and the pull-up resistors shown in FIG. 15.

In the middle right portion of FIG. 14, a resistor R10 connects the low-battery shutdown circuit to a motor voltage regulation circuit including transistors Q6, a second comparator U1, and a power transistor Q4. A fuse F1 is provided at the output for safety. The output of this circuit is a motor supply voltage $V_m$ which is preferably about 2.55 volts. Signals applied to the positive input of second comparator U1 shut down the circuit if a "RUNAWAY" condition is detected, i.e. the microprocessor cannot tell when the motor cycle is over.

In the center of FIG. 14B, a low-battery warning circuit, including a third comparator U1, detects when battery voltage goes below about 3.95 volts and provides an "early warning" signal to pin L7 (FIG. 15) of microprocessor 20, which can then actuate an alarm before actual shutdown occurs.

DOWNSTREAM OCCLUSION ALARM ("OCCL")

In the left middle of FIG. 14A, a downstream occlusion detector circuit, including an operational amplifier U4 and a fourth comparator U2, determines whether the peak of the pressure transducer 28 output signal exceeds the 1.2 volt reference voltage. If so, this indicates that piston 24 is encountering more-than-usual resistance in compressing bellows 34. A piezo-electric ceramic transducer 28 is mounted at the end of the drive system cam follower or piston 24. During normal pumping, the piston remains in constant contact with the cassette bellows 34, thus producing an electrical potential across the plates of the piezo-electric transducer 28. This signal varies in amplitude with the change in force required to compress the bellows. The transducer signal is fed directly through a high-impedance voltage divider network and a low-pass filter. This reduces the signal level to a usable operating range and eliminates any unwanted noise caused by motion artifact. The transducer signal is fed into amplifier U4, Preferably a model TLC271, whose gain is adjusted by a potentiometer P2.

The signal is then compared with a 1.2-volt fixed reference voltage. Under normal operating conditions, the transducer signal falls below the 1.2-volt reference, thus causing the output of fourth comparator U2 to remain HIGH. If a downstream occlusion is present, the amount of force required to compress the bellows 34 increases. This causes the transducer output signal to increase. If the transducer level is greater than the 1.2 volt reference voltage, the output of comparator U2 will trigger LOW. An occlusion signal is supplied to pin 2B (FIG. 15) of the multiplexer for transmission to microprocessor 20, which is preferably programmed to respond when a minimum of 2 motor cycles and/or 45 seconds have passed without relief of the blockage.

UPSTREAM OCCLUSION ALARM ("OCCL")

Above the aforementioned downstream occlusion detector circuit, FIG. 14A shows a combination upstream occlusion and "cassette not present" detection circuit, including fifth comparator U2. This measures whether the transducer output bell curve exists or is later than usual with respect to the motor cycle. If so, a warning signal is provided to pin 3B (FIG. 15) of the multiplexer for transmission to microprocessor 20. The piezo-electric ceramic transducer is used to detect the presence of an upstream occlusion. During normal pumping, the piston 24 remains in constant contact with bellows 34.

When an upstream occlusion, e.g. caused by an obstruction, fluid coagulation, or pinched tubing, occurs the bellows fails to return to its natural state and to make contact with the piston. As the pump unit commences its next pumping cycle, there is a slight delay between the time the motor turns on and the time piston 24 makes contact with the already-compressed bellows 34. This time delay is monitored by comparator U2, and thence by microprocessor 20.

CASSETTE NOT PRESENT ALARM ("EMPTY")

During normal pumping, and even when an upstream or downstream occlusion occurs, piston 24 at some point makes contact with bellows 34, generating an output signal from transducer 28. If there is no cassette properly latched into the cassette-receiving chamber, the transducer output signal remains at 0 volts. Therefore, the output of comparator U2 remains HIGH throughout the pumping cycle, which causes microprocessor to generate an "EMPTY" visual and audible alarm within two pumping cycles.

At top left of FIG. 14A, a circuit including transistors Q12, Q13, and Q5 shorts the motor terminals at the end of each cycle, as indicated by the reed switch discussed above, thereby causing a counter-electro-motive-force (EMF) to be generated in the motor windings, braking the motor.

FLUID EMPTY ALARM ("EMPTY")

At top right of FIG. 14A, a circuit including transistor Q10 turns on emitter 18 to test whether there is fluid in the cassette. In order to conserve power, emitter 18 is only activated during motor braking. Preferably, a GaAlAs plastic infrared emitter diode and an NPN phototransistor 19 are used in a through-beam configuration (FIG. 6) to detect the lack of fluid in the inlet chamber of the disposable cassette. A potentiometer, P1, controls the collector current of phototransistor 19. This allows for tolerances in the emitter/detector pairs 18, 19. A sixth comparator U2 compares the voltage drop across the phototransistor's emitter resistor to a fixed 1.2-volt reference voltage. The comparator's output is monitored by microprocessor 20. When there is liquid in the inlet chamber of the cassette, the output of comparator U2 is HIGH, the normal operating condition. When the cassette is pumped dry, the output signal goes LOW, triggering an alarm.

Another circuit, including transistor Q11 and a seventh comparator U2, controls actuation and loudness of a beeper, as ordered by VOLUME, RUNAWAY or BEEP signals from microprocessor 20 (see FIG. 15).

FIG. 15 is sheet 3 of the circuit diagram of the pump circuit. As previously noted, microprocessor 2 is preferably a masked Thomson/Mostek model with about 2 kilobytes×8 bits internal ROM and at least 128 bytes×4 bits internal RAM. The time-based counter mode is utilized with an internal divide-by-16 counter and an external 2-megahertz crystal to generate a clock signal for an 8-microsecond instruction cycle.

A multiplexer, preferably a CMOS (Complementary Metal Oxide Semiconductor) version of the National Semiconductor model 74HC257 2-data selector, is used to multiplex inputs to the microprocessor.

A restart circuit, comprising a resistor R16, diode D9, and capacitor C12, is connected to the reset pin of the microprocessor.

Output pin G2 of the microprocessor actuates the turning on of a backlight which illuminates the LCD display if the pump is operating on AC power or if the lightbulb logo switch on the front panel (FIG. 2) is pressed. The remainder of FIG. 15 will be self-explanatory to those skilled in the art.

Figure 16:
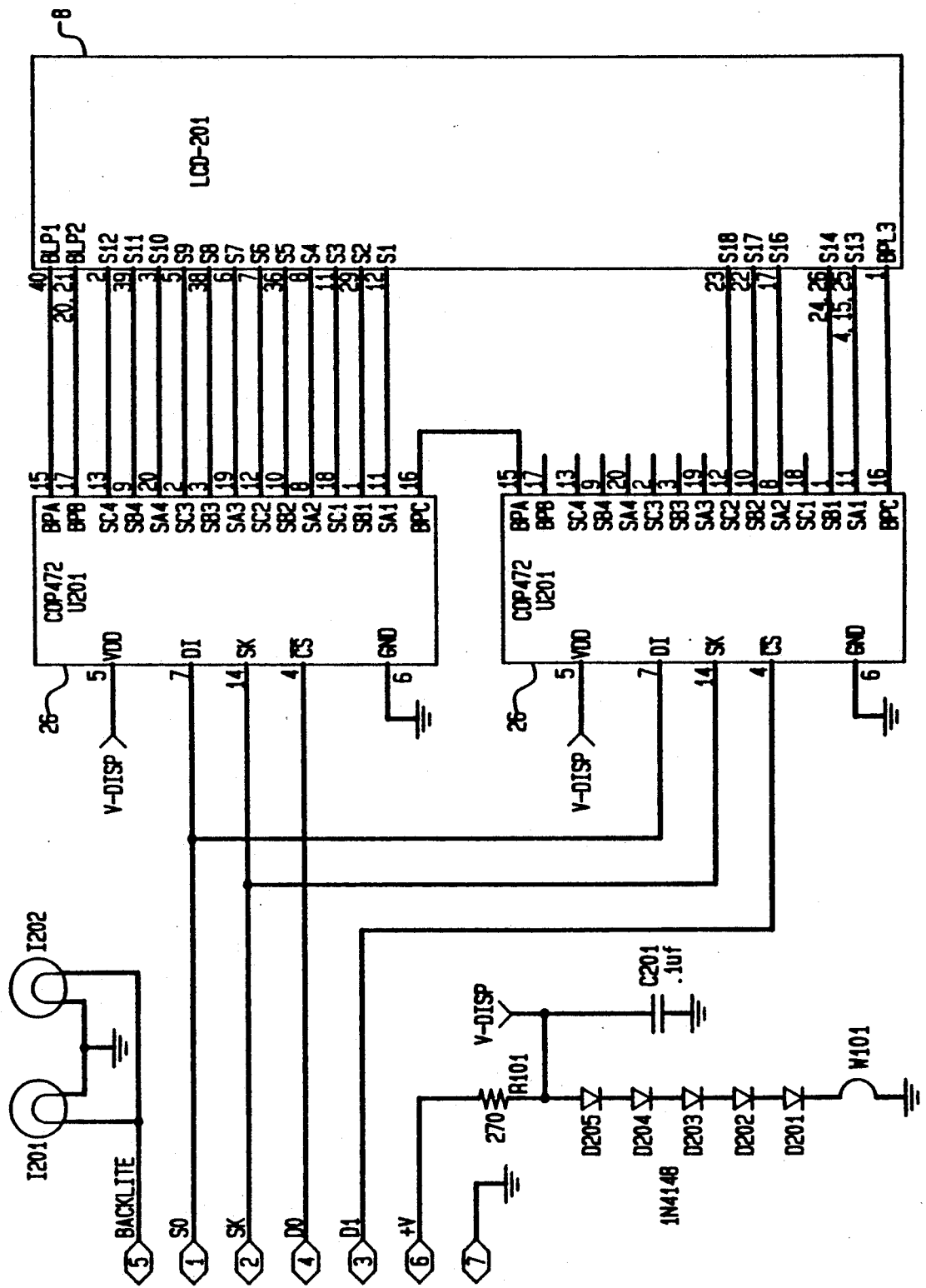

FIG. 16 illustrates the pin-out of the Liquid Crystal Display and its control chips, and their interconnections.

Figure 17:
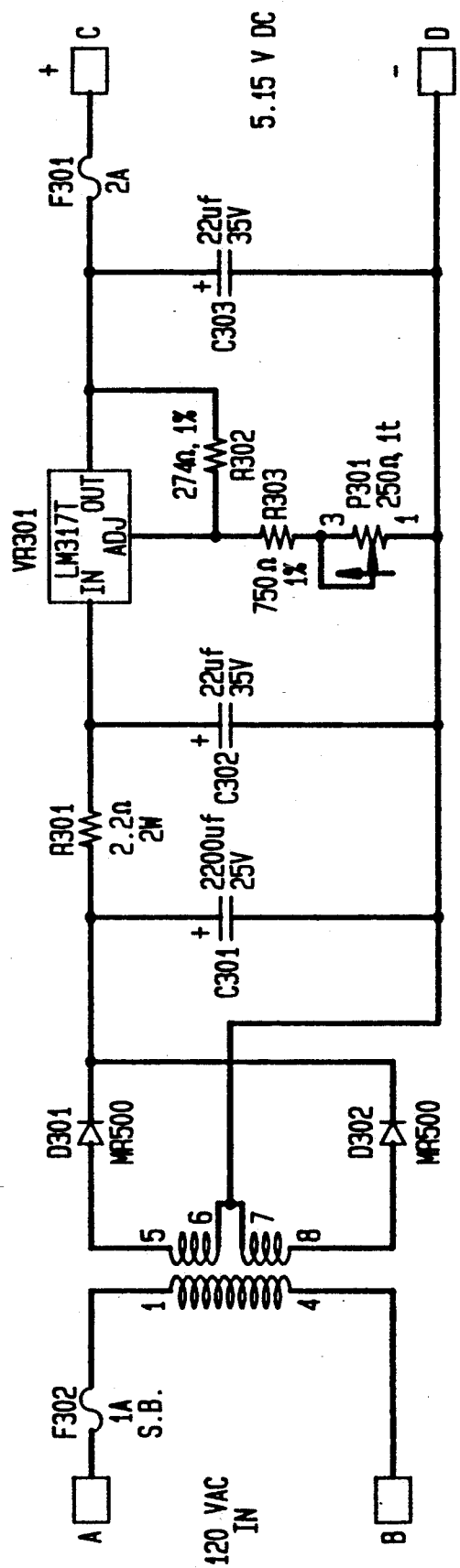
FIG. 17 is a circuit diagram of a power supply circuit which may be placed in a separate charger or backpack (not shown in this application) having means for receiving the pump and for clamping itself onto a pole.
Figure 18:
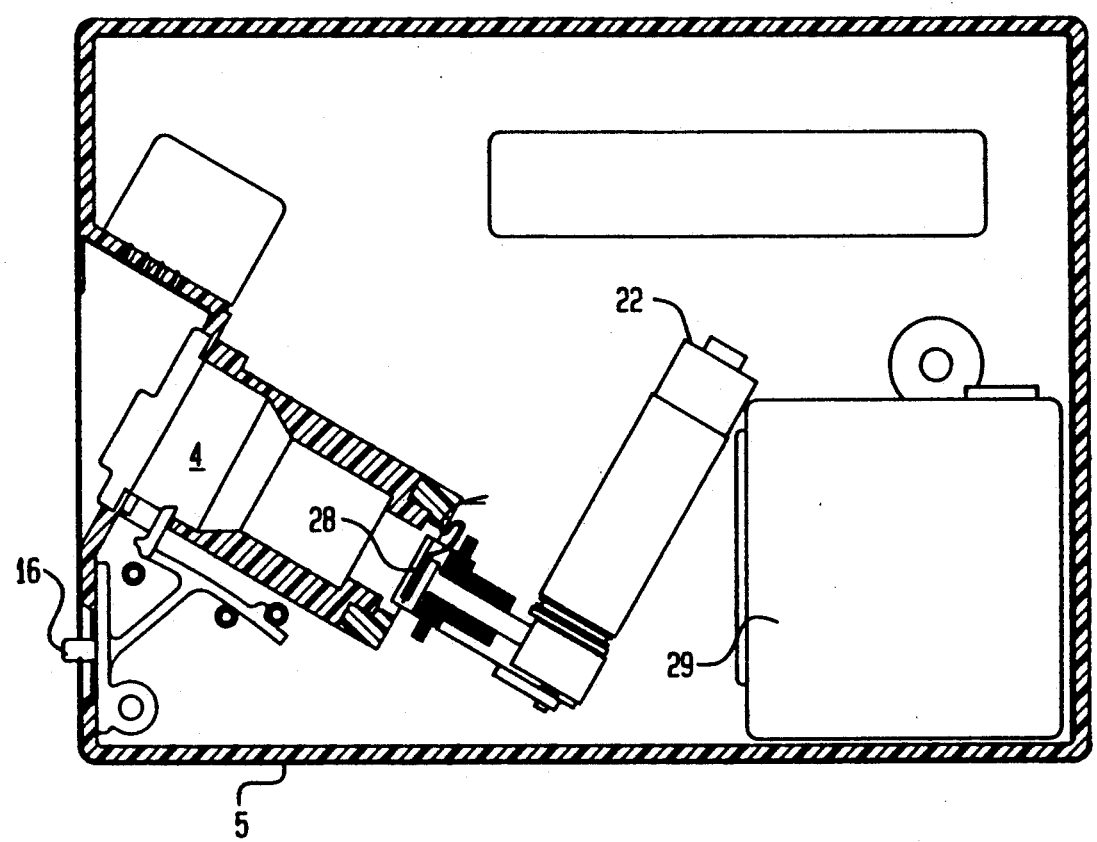
FIG. 18 is a schematic cross-sectional view showing the arrangement of the motor and piston in relation to the housing.

FIG. 17 is a schematic diagram of a power supply for use in operating the pump on A.C. power and in charging the internal rechargeable battery of the pump. Such a power supply is preferably housed in a backpack into which the pump housing can slide sideways. This backpack (not shown) includes a set of contacts which fit into the left side of the pump housing for power transmission purposes. The power supply includes a primary 1-amp slow-blow fuse, a transformer, a pair of diodes D301 and D302, an RC network, a voltage regulator, a 2-amp output fuse, and a pair of terminals supplying about 5.15 volts direct current for operating the pump or charging its battery.

The backpack preferably has a vertical slot in its back into which a standard hospital pole can be clamped by turning a knob on the side of the backpack and actuating a screw-driven clamp. The power supply circuit is itself supplied with power via an AC cord running from an outlet to the backpack.

Those skilled in the art will appreciate that numerous variations of the cassette and pump described above are possible within the scope of the inventive concept, and that the scope of the invention is not restricted to the embodiments described, but rather is defined by the appended claims.

We claim:

1. A readily sterilizable cassette, for use in a continuous pumping system having a supply tube (2), an outlet tube (6), and means (22,24) for intermittently applying pressure to said cassette, comprising:
    a hydraulically self-actuating inlet valve (44) communicating with said supply tube (2);
    a hydraulically self-actuating outlet valve (42) communicating with said outlet tube (6);
    a hollow, resilient, self-returning compressible member (34) having an interior communicating, for sterility reasons, only with said inlet and outlet valves; and
    a support structure (30,36,38) securing together said tubes, valves and compressible member in operating relation;
    said compressible member opening said outlet valve (42) and expelling fluid therethrough, in response to pressure from said means (22,24) for intermittently applying pressure, said compressible member (34) resiliently expanding in the absence of pressure from said means (22,24) for intermittently applying pressure, thereby opening said hydraulically self-actuating inlet valve (44) and drawing fluid from said supply tube (2).

2. The cassette of claim 1, wherein said inlet valve (44) and said outlet valve (42) comprise a unitary element (40).

3. The cassette of claim 2, wherein said unitary element (40) has a generally umbrella-shaped surface and a generally cylindrical axial stem (41), said outlet valve (42) being disposed in said stem, and an outer rim (45) of said umbrella-shaped surface forming said inlet valve (44).

4. The cassette of claim 2, wherein said compressible member is a bellows (34).

5. The cassette of claim 1, wherein said compressible member (34) defines a specific volume therewithin which is expelled upon each compression thereof.

6. The cassette of claim 1, wherein said compressible member is a bellows (34).

7. The cassette of claim 1, wherein said support structure comprises a bellows retainer (30) and a valve retainer (36) secured together.

8. The cassette of claim 7, wherein said retainers are secured together by sonic welding.

9. The cassette of claim 7, wherein said bellows (34) is generally cylindrical and formed with a peripheral rim at an open end thereof, and said bellows retainer (30) is formed with an annular chamber (32) receiving said peripheral rim.

10. The cassette of claim 7, wherein said support structure further comprises a cap (38) formed with cylindrical apertures interfitting with said supply tube (2) and said outlet tube (6).

11. The cassette of claim 7, wherein said valve retainer (36) is formed with a retaining lip for positioning and latching said cassette within a pump housing.

12. The cassette of claim 1, wherein said support structure (30,36,38) comprises a rigid thermoplastic material.

13. The cassette of claim 1, wherein said outlet valve (42) comprise a duck-bill valve.

14. The cassette of claim 1, wherein said inlet valve comprises an umbrella-shaped flexible element (44,45) in a bowl-shaped chamber (31).

15. The cassette of claim 1, wherein said cassette includes means (38) having an irregular shape which fits into a pump housing (5) only in a unique, correct orientation.

16. The cassette of claim 15, wherein said means (38) having an irregular shape is formed with means for gripping.

17. A readily sterilizable cassette, for use in a pumping system having a supply tube (2), an outlet tube (6), and means (22,24) for intermittently applying pressure to said cassette, comprising:
    an optical path formed in said cassette and having variable transmission properties, depending upon whether said supply tube (2) contains fluid, thereby permitting external detection (18, 19) of fluid supply exhaustion;
    a hydraulically self-actuating inlet valve (44) communicating with said supply tube (2);
    a hydraulically self-actuating outlet valve (42) communicating with said outlet tube (6);
    a hollow, resilient, self-returning compressible member (34) having an interior communicating, for sterility reasons, only with said inlet and outlet valves; and
    a support structure (30,36,38) securing together said tubes, valves and compressible member in operating relation;
    said compressible member opening said outlet valve (42) and expelling fluid therethrough, in response to pressure from said means (22,24) for intermittently applying pressure, said compressible member (34) resiliently expanding in the absence of pressure from said means (22,24) for intermittently applying pressure, thereby opening said hydraulically self-actuating inlet valve (44) and drawing fluid from said supply tube (2).

18. In a pumping system having a supply tube (2), an outlet tube (6), and a cassette (3) including
    a hydraulically self-actuating inlet valve (44) communicating with said supply tube (2);
    a hydraulically self-actuating outlet valve (42) communicating with said outlet tube (6);
    a hollow, resilient compressable member (34) having an interior communicating with said inlet and outlet valves; and a support structure (30,36,38) securing together said tubes, valves and compressible member in operating relation;

and means (22, 24) for applying pressure to said cassette, a method of pumping, comprising the steps of repeatedly providing a supply of fluid in said supply tube (2);

applying pressure to compress said compressible member (34);

permitting said compressible member to resiliently expand, thereby opening said hydraulically self-actuating inlet valve (44) and causing fluid to flow from said supply tube (2) into said compressible member (34); and again applying pressure to said compressible member (34), thereby closing said inlet valve (44) while opening said outlet valve (42) and causing fluid to flow from inside said compressible member (34) into said outlet tube (6).

* * * * *